United States Patent [19]

Allred, III et al.

[11] Patent Number: 4,762,119
[45] Date of Patent: Aug. 9, 1988

[54] SELF-ADJUSTING STEERING MECHANISM FOR BORESCOPE OR ENDOSCOPE

[75] Inventors: Jimmie B. Allred, III, Skaneateles; Allan I. Krauter, Syracuse, both of N.Y.

[73] Assignee: Welch Allyn, Inc., Skaneateles Falls, N.Y.

[21] Appl. No.: 78,712

[22] Filed: Jul. 28, 1987

[51] Int. Cl.⁴ .............................................. A61B 1/00
[52] U.S. Cl. ....................................... 128/4; 138/120
[58] Field of Search ............................ 128/4, 5, 6, 7; 138/120

[56] References Cited

U.S. PATENT DOCUMENTS

| | | | |
|---|---|---|---|
| Re. 31,289 | 6/1983 | Moore et al. | 128/6 |
| Re. 31,290 | 6/1983 | Moore et al. | 128/6 |
| 3,060,972 | 10/1962 | Sheldon | 138/120 |
| 3,162,214 | 12/1964 | Beazinet, Jr. | 138/120 |
| 3,190,286 | 6/1965 | Stokes | 128/6 |
| 3,266,059 | 8/1966 | Stelle | 138/120 X |
| 3,557,780 | 1/1971 | Sato | 128/4 |
| 3,583,393 | 6/1971 | Takahashi | 128/4 |
| 3,610,231 | 10/1971 | Takahashi | 128/6 |
| 3,669,098 | 6/1972 | Takahashi | 128/6 |
| 3,739,770 | 6/1973 | Mori | 128/6 |
| 3,799,151 | 3/1974 | Fukaumi et al. | 128/6 |
| 4,108,221 | 8/1978 | Freimuth et al. | 141/146 |
| 4,347,837 | 9/1982 | Hosono | 128/6 |
| 4,351,323 | 2/1982 | Ouchi et al. | 128/4 |
| 4,432,349 | 2/1984 | Oshiro | 128/4 |
| 4,651,718 | 3/1987 | Collins et al. | 128/4 |
| 4,655,257 | 4/1987 | Iwashita | 138/120 |

*Primary Examiner*—William H. Grieb
*Attorney, Agent, or Firm*—Wall and Roehrig

[57] ABSTRACT

In a cable-steerable endoscope or borescope, in which opposing cables are displaced to deflect the tip of the endoscope or borescope, a self-adjusting mechanism in the control section ensures a maximal differential force and a minimal total force is applied to the two steering cables. The self-adjusting mechanism has a frame that is affixed within the control section and a slider that is slidably disposed on the frame. First and second arms project outwardly from the slider and engage ends of the cable sheaths for the steering cables. The slider has a structure that engages the frame when there is no force on one steering cable to lock the slider against sliding motion, but which permits the slider to move proximally on the frame when there are forces applied on both steering cables. This arrangement, along with a reset spring, automatically takes up play or slack in the cable when it is not necessary, and also avoids simultaneous tensioning of the two cables which produces high steering forces that can damage the steering section.

15 Claims, 2 Drawing Sheets

SELF-ADJUSTING STEERING MECHANISM FOR BORESCOPE OR ENDOSCOPE

BACKGROUND OF THE INVENTION

This invention relates to a controllably bendable tube assembly, especially a borescope or endoscope of the type having a cable-actuated hollow steering section.

An endoscope is generally characterized as an elongated flexible tube, i.e. an insertion tube, with a viewing head at its distal or forward end, and a control section at its proximal end for controlling or steering the distal end. In such an endoscope, a bendable tube steering section is situated at the distal end adjacent to the viewing head. One or two pairs of control cables extend through the bendable tube section and the remainder of the insertion tube and connect with a steering control in the control section. One or both pairs of these cables are differentially displaced for bending the steering section to facilitate the inspection of an object.

An endoscope is typically inserted into the cavity of a patient in order to visually investigate the tissues within the cavity. For example, an endoscope can be inserted into the colon, stomach, or into the lung of a patient. Because the esophagus, bronchii, and colon are narrow, tortuous passageways, the steering section must be bent rather precisely, and as close to the viewing head as possible, in order to obtain the necessary penetration without damaging the patient's tissues. It is most desirable that both the cable tension be limited and that cable slack be minimized.

A borescope is a similar device, but intended for visual inspection of a mechanical assembly, such as a jet engine or turbine, where it would be difficult or impossible otherwise to examine the assembly's internal elements. The borescope needs to be insertable into narrow tortuous passageways, and must observe similar steering and bending considerations.

A number of types of steering mechanisms are known. For example, helically coiled strips are employed in endoscopes or borescopes as described in U.S. Pat. Nos. 3,610,231 and 3,739,770. Steering sections formed of thin-walled cylindrical segments or bands that are joined by means of pins or bifurcations, or other similar articulations such that the segments are rockable on one another, are described in U.S. Pat. Nos. 3,583,393; 3,669,098; 3,799,151; and 4,347,837. U.S. Pat. No. 3,557,780 describes an endoscope steering section formed of two flexure portions, with two sets of control wires. Stays or flexible backbone members of various lengths control the degree of curving and the location of the curvature on the steering section.

An endoscope described in the U.S. Pat. No. 3,799,151, has cylindrical segments articulated in one plane or another plane as required to select the amount and direction of bending of the endoscope steering section.

For those steering sections that are bendable in two planes, a significant amount of cable slack is typically included so that the steering cables for one plane do not bind when the steering section is bent in the other plane. Some cable slack is also included to accommodate cable tightening due to coiling and bending of the insertion tube through which the steering cables pass.

In a steerable endoscope or borescope, opposing steering cables are displaced to deflect its distal tip. For optimum steering, these cables are differentially displaced. That is, as one cable is pulled away from the steering section, the other moves towards the steering section. However, the motion of the one cable is not normally the exact opposite of the motion of the other. Coiling of the insertion tube and steering can result in the tensioning, at the same time, of both cables of an opposed pair. This simultaneous tensioning produces friction, resulting in high steering forces that can damage the steering section or cables, leading to early failure. Adding cable play or slack can alleviate this problem, but can create other problems of its own, such as imprecise steering. Moreover, large steering knob movements are then required for deflection of the endoscope or borescope tip.

OBJECTS AND SUMMARY OF THE INVENTION

Accordingly, it is an object of this invention to provide a borescope or an endoscope which avoids the drawbacks of the prior art.

It is a more specific object of this invention to provide a cable bendable borescope or endoscope that has a minimal amount of slack and that is easy to deflect, even when the insertion tube section is coiled or the steering section is fully deflected in another plane.

It is another object of this invention to minimize or eliminate the need for cable adjustment in endoscopes or borescopes.

It is a further object of this invention to maximize the net or differential force in the opposed pair of steering cables while minimizing the collective or total force in the pair of cables.

It is a still further object of this invention to provide a release mechanism which accomplishes the above objects, but which is simple in design and can be housed in the control section housing.

As aforesaid, the ideal self-adjusting mechanism should ensure that there is maximal differential force and minimal collective force applied to the steering cables of an opposed pair. To achieve this, one of the cables should have zero force during steering. To this end, the self-adjusting mechanism has a frame fixedly mounted within the control section and including a track that is axially oriented, i.e., along the direction of cable motion. A slider is disposed to slide axially along the frame, i.e., in the direction of cable motion.

First and second arms project outwards from the slider and engage the ends of the cable sheaths for a set of steering cables, but do not interfere with motion of the cables themselves. The slider has a brake mechanism which engages the frame when there is no force in one steering cable and locks the slider against sliding motion relative to the frame. When there is tension in both cables, the brakes release, allowing the slider to slide proximally along the frame, releasing cable tension. A reset spring urges the slider distally when no steering forces are present in either cable. The first and second arms can include a spring or the like for biasing the arms for motion relative to the slider body for normally placing the slider in its engaged condition.

In one preferred embodiment, the frame includes two rods arranged parallel to the steering cable, with the slider being a block with axial bores that the two rods fit through. First and second spring arms are mounted on the distal end of the slider and these have inner holes which correspond to the positions of the rods and outer holes which correspond to the positions of the cable sheaths. There are adjusting nuts on each sheath end which engage the spring arms. If there is no force in one cable and thus in the corresponding cable sheath, that cable sheath will release the respective spring arm, and the arm will contact the associated rod and lock against it, preventing motion of the slider. If there is some force in both the cables, and the cable sheaths, the cable sheaths will move both spring arms in the same (proximal) direction, and unlock the slider so that it moves with them. This mechanism also moves the cable sheath ends distally when there is zero force in both cables, so as to take up cable slack when slack is not required. This translates a maximum amount of cable motion into steering deflection.

The above and many other objects, features and advantages of this invention will be more fully understood from the ensuing detailed description of some exemplary preferred embodiments of the invention, which description should be read in connection with the accompanying drawing.

DETAILED DESCRIPTION OF THE PREFERRED EMBODIMENTS

Figure 1:
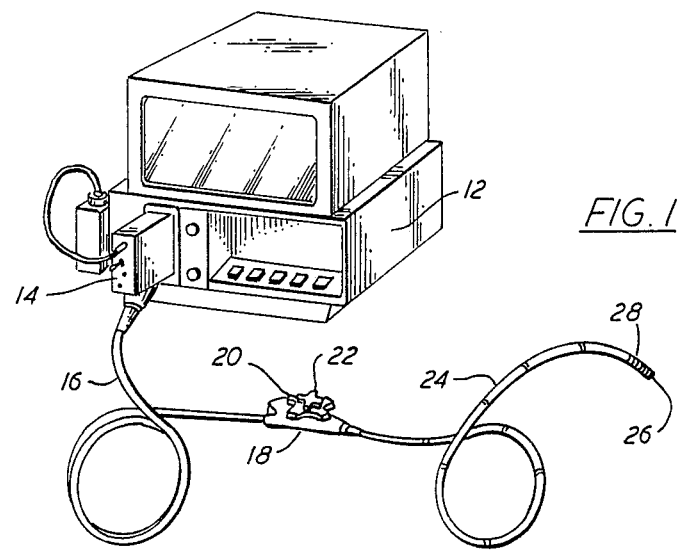
FIG. 1 is a perspective view of a video endoscope of the type which can employ the self-adjusting steering mechanism of this invention.
Figure 2:
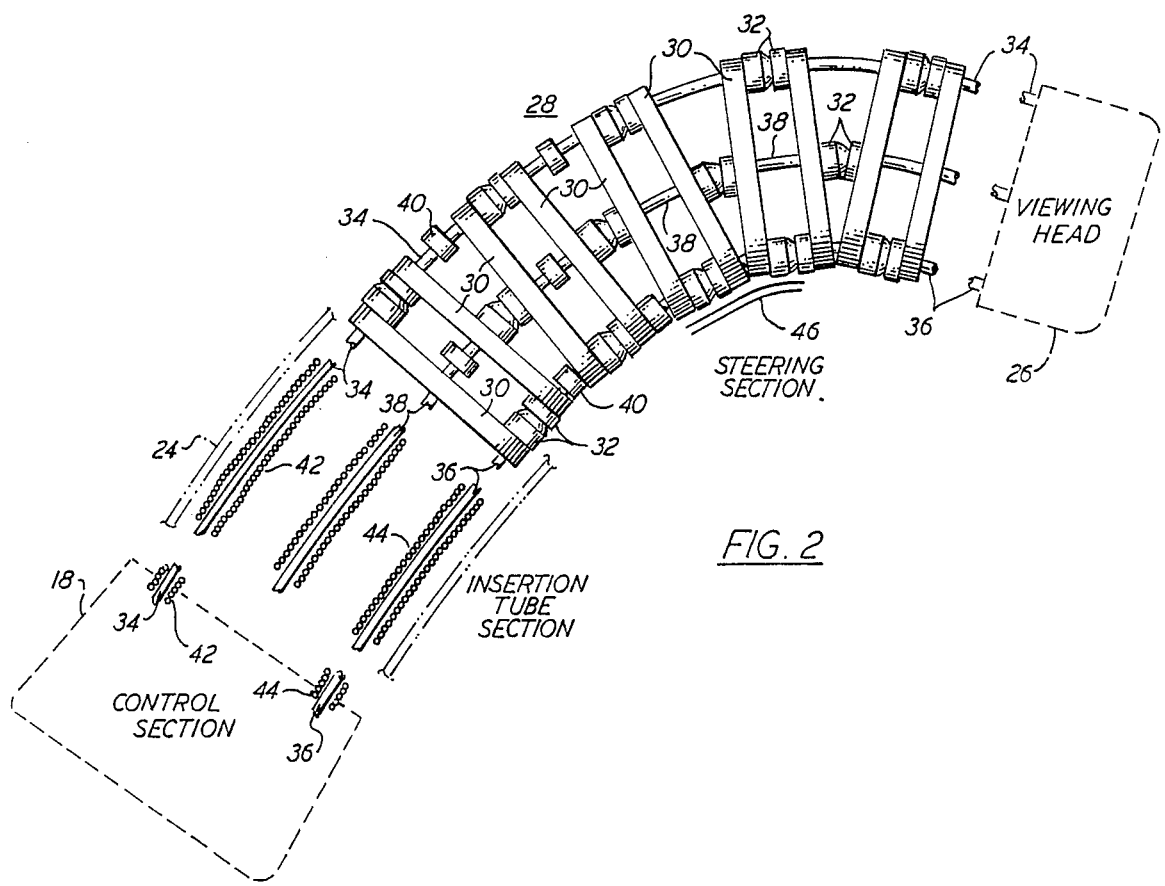
FIG. 2 is a schematic view, partly cut away, of a cable-type steering section of the endoscope of FIG. 1.

With reference to the drawing, FIG. 1 shows a video endoscope system 10, having a video monitor and console 12, with a connector adaptor 14 that connects the console 12 through an umbilical 16 to an endoscope control unit 18. The control unit 18 has a pair of steering knobs 20 and 22 for deflecting the endoscope tip in the upwards-downward direction and in the left-right direction, respectively. An elongated flexible insertion tube 24 extends from the control unit and has at its tip a viewing head 26 that contains illuminating and video pick-up devices. Just to the proximal side of the viewing head 26 is a steering section 28, which is of the cable-actuated type of which an example is shown in FIG. 2. It is noted that many such steering mechanisms exist, as described in the patents identified earlier. Endoscopes of this general design are described, e.g., in U.S Pat. Nos. Re 31,289 and Re 31,290, each of June 28, 1983.

Borescopes are of similar design, but typically with longer insertion tubes.

With reference to FIG. 2, a steering section 28 is shown of the type described in commonly-assigned Pat. applications Nos. 806,667, and 07/078,713.

Other articulated cable-type steering mechanisms are described in U.S. Pat. Nos. 3,610,231; 3,739,770; 3,583,393; 3,669,098; 3,779,151; 4,347,837; 3,557,780; 3,062,972; 4,108,221; and 3,190,286.

In FIG. 2 the steering section 28 is formed of a stack of apertured washers 30, sometimes called vertebrae or discs, which are separated by an arrangement of spacer beads 32. To effect upward-downward deflection of the viewing head 26, an upper steering cable 34 and a lower steering cable 36 penetrate through opposite sides of the washers 30 and through the associated spacer beads 32, and are affixed onto the viewing head 26. These cables 34 and 36 extend back through the insertion tube 24 to the control section 18. Also shown is another cable 38 (its opposing associated cable is obscured in this view) for controlling right-to-left steering. Limiter beads 40 are disposed on the cable at selected locations to limit the amount of bending of the steering section, especially at the proximal end thereof.

Within the insertion tube 24, the cables 34 and 36 run through cable sheaths 42 and 44 respectively, which are flexible but which resist axial compression. Thus, the cable sheaths 42 and 44 provide reaction forces for the forces on the cables 34 and 36, so that any cable motion is transferred from the control section 18 to the steering section 28.

The flexible insertion tube 24 terminates at the steering section 28. A flexible outer covering 46 covers the steering section 28 and is attached to the insertion tube 24 and to the viewing head 26. The cable sheaths 42 and 44 are anchored at the proximal side of the steering section 28 and extend into the control section 18. The cables 34, 36 are themselves anchored in the viewing head 26, and the proximal ends thereof are connected to a windlass arrangement (not shown) in the control section 18.

Figure 3:
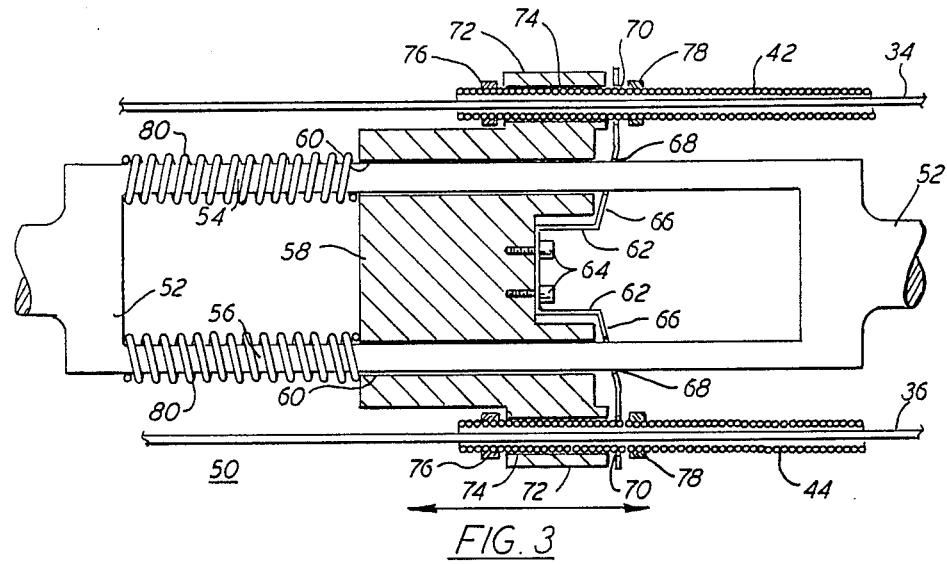
FIG. 3 is a schematic sectional view of a self-adjusting mechanism according to a first embodiment of the invention.

As shown in FIG. 3, a self-adjusting mechanism 50 according to one preferred embodiment of this invention has a frame member 52 affixed inside the housing of the steering section 18. This frame member 52 is comprised of upper and lower rods 54 and 56 which extend in the axial direction, i.e., parallel to the cables 34 and 36. A slider block 58 is fitted onto the frame member 52 to slide on the rods 54, 56, and to this end it has a pair of axial bores 60 through which the upper and lower rods 54 and 56 respectively pass. A pair of spring arm members 62 are affixed by bolts or machine screws 64 to the distal side of the block 58. Each spring arm member 62 has a slanted portion that extends radially outward, i.e., laterally and somewhat distally, and has a hole or aperture 68 which fits over the associated one of the upper and lower rods 54 and 56. At an outer end of each of the spring arms 62 is an outer hole 70 which fits over the associated upper or lower cable sheath 42, 44.

The slider block 58 has a pair of lateral protuberances 72 aligned with the spring arms 62 and each of which has an axial bore 74 through which the associated cable sheath 42, 44 passes. On each cable sheath 42, 44, an adjusting nut 76 is attached at the proximal side of the protuberance 72 and another adjusting nut 78 is attached at the distal side of the spring arm member 62.

Compression reset springs 80 are placed around rods 54 and 56 and between the proximal face of slider 58 and frame member 52. These springs 80 tend to urge the slider 58 in the distal direction.

Because of the angles of the slanted portions 66 of the spring arms 62 relative to the rods 54 and 56, the slider block 58 can move distally as long as there is no force in the two sheaths 42 and 44. Motion to the proximal side is prevented because the spring arms 62 lock up against the rods 54 and 56. Bias in the spring arms 62 against the rods 54 and 56 maintains an arm-rod contact to ensure locking action.

The spring arms 62 and the slider 58 receive the cable sheaths 42, 44 in the manner described above, and these sheaths 42, 44 pass freely through the holes 70 in the spring arms and through the bores 74 in the slider protuberances 72. The cables 34, 36 pass through the sheaths 42, 44 in the usual fashion and exit proximally through the sheath ends at the slider block 58. The distal adjusting nuts 78 allow the sheaths to push the spring arms 62 proximally. The proximal adjusting nuts 76 allow the sheaths 42, 44 to pull the slider block 58 distally.

The self-adjusting mechanism 50 operates as described hereafter, considering first, for purposes of illustration, steering in the upward direction (in the drawing) and thereafter steering in the downward direction.

Initially, the upper cable 34 is tightened, which causes the upper sheath 42 to push against the upper spring arm 82, moving the same proximally. This releases the upper spring arm 82 from the rod 54 so that the slider block 58 can move proximally (i.e. to the left of the drawing). If there is no force at that time applied to the lower cable 36, the lower spring arm 84 will lock onto the lower rod 56. At that point, steering in the upward direction continues.

However, if there is simultaneously a force applied to the lower cable 36, the associated force will tend to displace the lower cable sheath 44, and the adjusting nut 78 thereof contacts the lower spring arm 84 and releases it from the lower rod 56. The slider block 58 thereafter moves in the proximal direction (i.e., to the left in the drawing). At such time as the force in the lower cable 36 disappears, the lower spring arm 84 locks onto the lower rod 56 and prevents further motion of the slider block 58. This movement of the slider block 58 relieves collective tension in the cables 34 and 36, and after the locking of the slider block 58, steering in the up direction is resumed.

With the endoscope viewing head 26 deflected upwards, steering in the downward direction is effected by displacing the cable 34 distally and pulling the cable 36 proximally. Here, steering from the point of maximal upward deflection first reduces the force in the upper cable 34 and its cable sheath 42 to zero. At that point, with tension in both cables at zero, the slider block 58 can move in the distal direction (to the right in the drawing) because of the springs 80 and because of any tension forces on the sheath, as these act through the proximal adjusting nuts 76 and tend to pull the slider block 58 distally. This movement unlocks the spring arms 62 and takes up cable slack. Later, when steering forces appear on the lower steering cable 36 and the lower cable sheath 44, the distal motion of the slider block 58 ceases, the upper spring arm 82 locks onto the upper rod 54 if no forces exist on the upper cable and upper sheath 42, and downward steering continues. Any simultaneous force in the upper cable 34 and sheath 42 again releases the slider block 58 to permit it to move in the proximal direction.

As is evident from the above explanation, the self-adjusting mechanism 50 is symmetrical in operation, and its action for downward steering is the same as for upward steering.

Figure 4:
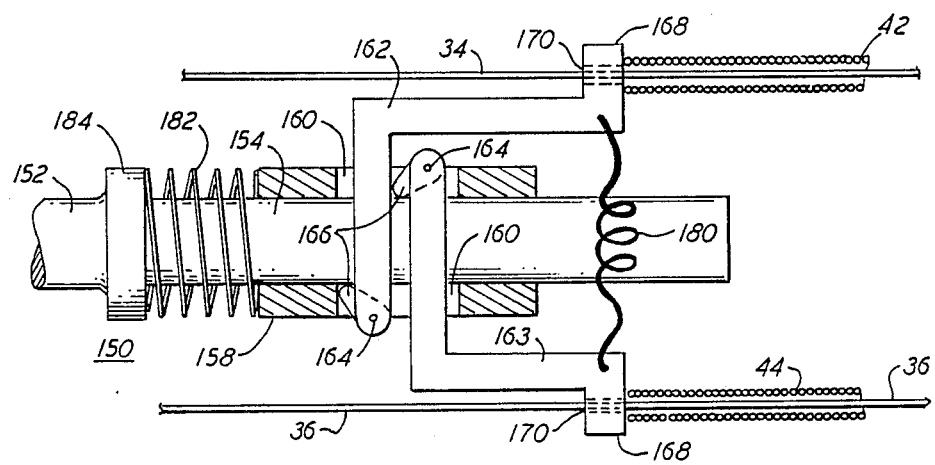
FIG. 4 is a schematic sectional view of a self-adjusting mechanism according to a second embodiment of the invention.

A self-adjusting mechanism 150 according to a second embodiment of this invention is shown in FIG. 4. In this embodiment, parts that correspond to elements of the first embodiment are identified with the same reference numbers. In this embodiment the self-adjusting mechanism 150 comprises a frame 152 mounted within the control unit 18, and has a longitudinal frame slide 154. A slider 158 of generally cylindrical construction slides on the frame slide 154 and has openings 160 on lateral surfaces thereof. A generally L-shaped upper arm 162 is pivoted at the lower opening 160 and extends across the frame slide 154, through the upper opening 160, and then axially in the distal direction. A lower L-shaped arm 163 similarly extends out the lower opening 160 and thence axially in the distal direction. The pivot ends of these arms 162 and 163 are mounted on pivot pins 164 and each pivot end has a cam 166 that is angled slightly to the back or proximal direction. Each L-shaped arm 162, 163 has an outward protuberance 168 at its free end, on which the respective cable sheath 42 or 44 can be mounted, and each protuberance 168 has a bore 170 therethrough which allows free passage of the respective steering cable 34 or 36. A bias spring 180 biases the free ends of the arms 162 and 163 towards each other, while a coil compression reset spring 182 acts between the proximal end of the slider 158 and a flange 184 on the frame 152.

The operation of this mechanism 150 is basically as follows.

The slider 158 is generally free to move along the frame slide 154. However, the cams 166 that are rigidly connected to the arms 162 and 163 act such that motion of the slider 158 in the proximal direction (that is, towards the control section) tends to lock the cams 166 and thereby stop the slider motion. The bias spring 180 ensures such locking by maintaining cam-frame contact. Distal motion of the slider 158, that is, to the right in the drawing, tends to release the cams 166, so that motion can take place easily. The reset spring 182 tends to urge the slider 158 in the distal direction.

When the upper cable 34 is tightened, i.e., in the sense to deflect the steering section 28 upwards, the upper sheath 42 urges the upper arm 162 in the proximal direction (i.e., to the left in the drawing). This releases the cam 166 to the upper arm 162 so that the slider 158 can move in the proximal direction. If there is at that time no force on the lower cable 36 the cam 166 on the lower arm 163 will tend to lock the slider 158 against the frame slide 154. However, if at that time there is a force on the lower cable 36, the associated force, as transmitted from the lower cable sheath 44 to the lower arm 163, tends to open the lower arm cam 166. Therefore, the force on the cable sheaths 42 and 44 tend to move the slider 158 proximally, (i.e. to the left in the drawing). When the force in the lower cable 36 disappears, the cam 166 on the lower arm 163 closes, as aided by the bias spring 180, against the frame slide 154 and prevents further sliding motion of the slider 158. After that, upwards steering or deflection can continue.

From an upward deflection state, the steering section 28 is steered or deflected downwards first by reducing the force in the upper cable 34 and its associated sheath 42 to zero. This permits the slider 158 to move distally (i.e. to the right) due to the urging of the reset spring 182 and due to any tension forces in the cable sheaths 42 and 44. Cable slack is thereby taken up. When steering forces appear in the lower cable 36 and lower cable sheath 44, the distal motion of the slider 158 stops, the cam 166 on the upper arm 162 locks against the frame slide 154, and downward steering continues. If there should be a simultaneous force at the upper cable 34 and upper cable sheath 42, the cable sheath force again releases the slider 158 to permit it to move in the proximal direction. The operation of the mechanism 150 is symmetrical, and is the same for downward steering as for upward steering.

Figure 5:
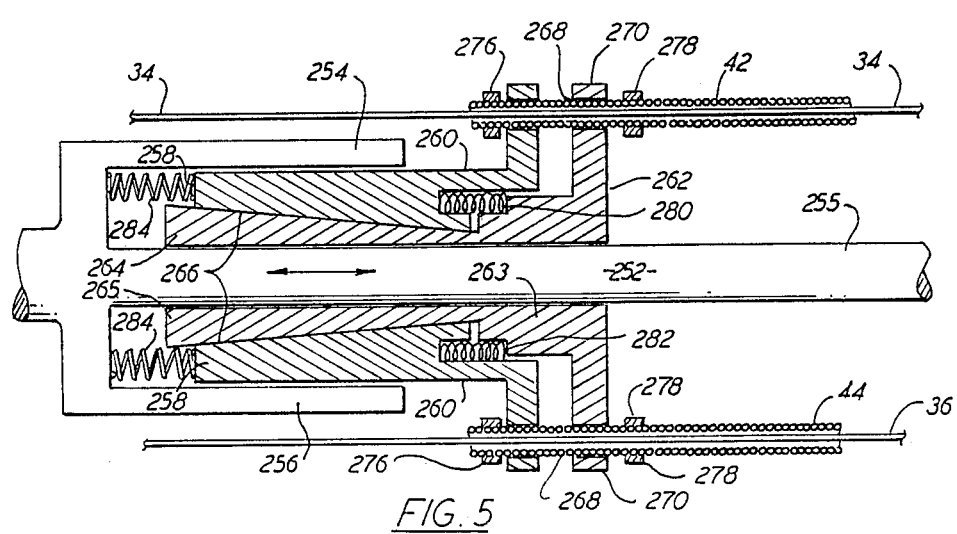
FIG. 5 is a schematic sectional view of a self-adjusting mechanism according to a third embodiment of the invention.

A self-adjusting mechanism 250 according to a third embodiment of this invention is illustrated in FIG. 5.

Here, a frame member 252 which is fixed relative to the housing of the steering section 18 has an upper longitudinal member 254, a central longitudinal member 255, and a lower longitudinal member 256. A slider 258 slides relative to the upper and lower longitudinal members 254 and 256 and has outer surfaces 260 which face against these upper and lower frame members 254 and 256. An upper arm member 262 and a lower arm member 263 slide generally with the slider 258 and against the central longitudinal frame member 255. The arms 262 and 263 have respective inclined planes 264 and 265 which face against associated inclined planes 266 of the slider 258. The arm members 262 and 263 have respective bores in lateral protruding parts 270 thereof. The slider 258 has similar protruding parts 272 with bores or apertures 274 which align in registry with the bores 268 of the arm members 262 and 263. The sheath 42 of the upper cable 34 extends through the bores 268 and 274 of the upper arm 262 and slider 258, while the sheath 44 of the lower cable 36 extends through the bores 268 and 274 of the lower arm 263 and slider 258. The cable sheaths 42 and 44 are freely slidable in these apertures, and are held by respective adjusting nuts 276 on the sheaths 42 and 44 proximally of the slider bores 274, and by adjusting nuts 278 disposed on the cable sheaths distally of the bores 268.

As is also shown in FIG. 5, a bias compression spring 280 acts in cooperation with the inclined plane 264 to wedge the upper arm 262 between the slider 258 and the central longitudinal member 255, while another similar bias compression spring 282 wedges the lower arm 263 between the slider 258 and the longitudinal member 255. Compression reset springs 284 are placed between the proximal face of the slider 258 and the frame 252. These springs tend to urge the slider in the distal direction.

As the slider 258 moves axially along the frame member 252 the inclined plane surfaces 264, 265 and 266 act as ramps which mate the slider 258 and the arms 262 and 263 to effect lateral or radial movement. The inclined plane surfaces 264, 265 and 266 are arranged such that motion of the slider 258 towards the control section 18 tends to wedge or lock the arms 262 and 263 against the frame central member 255, and thereby stop such motion. The bias springs 280 and 282 ensure this locking by maintaining contact between the arms 262, 263 and the slider 258. Motion of the slider 258 in the distal direction tends to unlock or unwedge the mechanism 250, so that distal motion can continue and take place easily.

The cable sheaths 42 and 44 move freely through the holes 268, 274 in the arms and slider, and the distal nuts 278 allow the sheaths 42, 44 to push the arms 262, 263 proximally, while the proximal adjusting nuts 276 allow the sheaths 42, 44 to pull the slider 258 distally.

Considering a steering operation for steering in the upwards direction, when the upper cable 34 is tightened, the upper sheath 42 moves proximally (i.e., to the left in the drawing) so that the distal adjusting nut 278 urges the upper arm 262 proximally (i.e. to the left). This releases the wedging on the upper arm 262 so that the slider 258 can also move proximally. If there is at the same time no force on the lower cable 36, the lower arm 263 wedges against the slider 258 and the central longitudinal frame member 255, and locks the slider 258 against motion. Further movement of the cable 34 continues the upward steering. However, if there is a simultaneous force on the lower cable 36, the reaction force on the lower cable sheath 44, which is transmitted from the distal adjusting nut 278 to the lower arm 263, relieves the wedging force on the slider 258 and the central longitudinal frame member 255, so that further movement of the slider 258 on the frame 252 continues. When the force on the bottom or lower cable 36 disappears, the lower arm 263 locks between the slider 258 and the central longitudinal frame member 255, as aided by the bias spring 282. This prevents further motion of the slider 258 in the proximal direction. Then, from that time, the force on the cable 34 tends to resume steering in the upwards direction. From this point, where the endoscope is deflected in the upwards direction, steering in the downwards direction first reduces force in the upper cable 34 and upper sheath 42 to zero. The slider 258 then moves distally (i.e. to the right) because of the compression reset springs 284 and because of any sheath tension forces which are transmitted from the cable sheath 42 and 44 through the proximal adjusting nuts 276 to the slider 258. These forces urge the slider distally and unlock the wedging of the slider 258 and the arms 262, 263. Cable slack is thereby taken up. When the lower cable 36 and lower cable sheath 44 begin to experience steering forces, the distal adjusting nut 278 on the lower cable sheath 44 presses against the lower arm 263. Motion of the slider 258 in the distal direction (i.e., to the right) ceases. At this time, the upper bias spring 280 causes the slider 258 and the upper arm 262 to wedge against each other and against the central longitudinal frame member 255 to lock the slider 258 against further motion. Further force on the cable 36 at this point deflects the endoscope steering section 28 downward. If there should be a simultaneous force in the upper cable 34, the reaction force on the upper cable sheath 42 again releases the slider 258 to move in the proximal direction, i.e. to the left. Again, as with the other embodiments, the action of this self-adjusting mechanism 250 is symmetrical for the two cables 34 and 36 of this pair of steering cables.

While not specifically shown here, a second self-adjusting mechanism 50, 150, or 250 would be employed with respect to the steering cable 38 and its mate (not shown) for steering in the horizontal plane.

While this invention has been described in detail with respect to certain preferred embodiments, it should be recognized that the invention is not limited to those embodiments. Rather, persons of ordinary skill in the art would recognize many possible modifications and variations that would not depart from the scope and spirit of this invention, which is to be defined in the appended claims.

What is claimed is:

1. In a steerable endoscope or borescope of the type having a viewing head, a cable-bendable steering section disposed proximally of the viewing head and including at least one pair of steering cables and bending means responsive to differential movement of the cables to bend the steering section, an insertion tube section proximally of the steering section through which said steering cables pass, and a control section proximally of said insertion tube section and which includes means for imparting a differential motion to said steering cables to bend said steering section, with said steering cables having respective cable sheaths extending thereover from said control section to said steering section to carry opposing forces to any forces applied to said steering cables;

the improvement wherein said control section includes a self-adjusting steering mechanism comprising a frame fixedly mounted in said control section and including axially oriented track means; slider means which enjoys axial sliding movement on said track means; first and second arms extending radially outward from said slider means and including means for engaging the proximal ends of said cable sheaths; and engaging means on said slider means for engaging said frame when the force in one said steering cable is zero to lock the slider means against proximal sliding motion on said frame, but permitting said proximal sliding motion when tension forces in both said steering cables exist.

2. The endoscope or borescope of claim 1 in which said first and second arms include resilient means biasing said arms with respect to said slider for normally placing said engaging means into an engaged condition.

3. The endoscope or borescope of claim 1 in which said frame includes a first rod and a second rod disposed generally in the direction parallel to said steering cables; said slider means includes a slider member having first and second axial bores therethrough which respectively overfit said first and second rods; and said first and second arms include first and second spring arm members mounted on said slider member and each having a first hole through which a respective one of the rods passes and a second hole through which a respective one of cable sheaths passes.

4. The endoscope or borescope of claim 3, wherein said spring arms slant outwards and distally at the locations of said first holes therethrough.

5. The endoscope or borescope of claim 3 wherein said slider member has cable bores aligned with the second holes of said spring arms, with said cable sheaths passing through the respective ones of said slider member cable bores and the spring arm second holes.

6. The endoscope or borescope of claim 5 in which said cable sheaths each have a proximal adjusting nut disposed proximally of said slider member cable bore, and a distal adjusting nut disposed distally of said spring arm.

7. The endoscope or borescope of claim 6 further comprising resilient means for biasing said slider means distally relative to said frame.

8. The endoscope or borescope of claim 1 in which said arms each include an L-shaped member pivotally mounted at one end on said slider means, with said cable sheaths mounted to respective free ends of said L-shaped arms, and resilient means biasing the free ends of the L-shaped arms being biased towards each other.

9. The endoscope or borescope of claim 8 wherein said engaging means includes first and second gripping cams mounted on the pivot ends of said first and second L-shaped arms.

10. The endoscope or borescope of claim 8 further comprising resilient means for biasing said slider means distally relative to said frame.

11. The endoscope or borescope of claim 1 in which said frame includes a central frame member and first and second outer frame members, the outer and central frame members extending generally parallel, said first and second arms having an inner side sliding on said central frame member and outer surfaces which form a ramp; said slider means includes a slider member having outer surfaces facing said first and second frame members and inner ramp surfaces to mate with the arm outer ramp surfaces; and bias spring means acting between said arms and said slider means to urge said arms to wedge said slider means against said frame members.

12. The endoscope or borescope of claim 11 in which said slider member is formed of upper and lower slider portions respectively associated with said first and second arms.

13. The endoscope or borescope of claim 12 in which each of said slider portions and said arms includes a radially projecting member through which an associated one of said cables passes.

14. The endoscope or borescope of claim 13 in which said cable sheaths pass through the radially projecting members of the associated slider portions and arms, and further including for each said sheath a distal adjusting nut disposed beyond the associated arm and a proximal adjusting nut disposed proximally of the projection of the associated slider portion.

15. The endoscope or borescope of claim 13 further comprising resilient means for biasing said slider means distally relative to said frame.

* * * * *